(12) United States Patent
Lange et al.

(10) Patent No.: US 6,537,588 B1
(45) Date of Patent: Mar. 25, 2003

(54) FOOD-INDUCED ANTISECRETORY PROTEINS IN EGG YOLK

(75) Inventors: Stefan Lange, Göteborg (SE); Leif Göransson, Kågeröd (SE); Ivar Lönnroth, Mölndal (SE)

(73) Assignee: Rural Patent Svenska AB, Stockholm (SE)

( * ) Notice: Subject to any disclaimer, the term of this patent is extended or adjusted under 35 U.S.C. 154(b) by 0 days.

(21) Appl. No.: 09/868,172
(22) PCT Filed: Dec. 14, 1999
(86) PCT No.: PCT/SE99/02340
§ 371 (c)(1),
(2), (4) Date: Jul. 6, 2001
(87) PCT Pub. No.: WO00/38535
PCT Pub. Date: Jul. 6, 2000

(30) Foreign Application Priority Data

Dec. 17, 1998 (SE) ................................................ 9804393

(51) Int. Cl.[7] .............................. A61K 35/54; A23L 1/32
(52) U.S. Cl. ..................... 424/581; 424/94.1; 426/614
(58) Field of Search ................................ 424/581, 94.1

(56) References Cited

U.S. PATENT DOCUMENTS 5,464,637 A    11/1995   Horikawa et al.

FOREIGN PATENT DOCUMENTS

| SE | 466331 | 1/1990 |
|----|--------|--------|
| WO | WO 97/08202 A1 | 3/1997 |
| WO | WO 98/21978 | 5/1998 |

OTHER PUBLICATIONS

Lange et al., *British Poultry Science*, vol. 35, 1994, pp 615–620.

Primary Examiner—Leon B. Lankford, Jr.
Assistant Examiner—Ruth A. Davis
(74) Attorney, Agent, or Firm—Burns, Doane, Swecker & Mathis, L.L.P.

(57) ABSTRACT

The invention generally relates to the use of natural antisecretory proteins (NASP) for the preparation of NASP-enriched functional food products or pharmaceutical products for the treatment and prophylaxis of disease-like conditions caused by extreme body fluid discharge. In particular, the invention relates to the use of NASP-enriched egg yolk as source of NASP.

11 Claims, No Drawings

FOOD-INDUCED ANTISECRETORY PROTEINS IN EGG YOLK

FIELD OF INVENTION

The present invention generally relates to use of natural antisecretory proteins (NASP) for the preparation of NASP-enriched functional food products and pharmaceutical products for the treatment and prophylaxis of abnormal physiological conditions caused by exceptionally high levels of body fluid discharge. In particular, the invention relates to the use of egg yolk having been enriched with NASP, for the preparation of such products. The invention also relates to food products and pharmaceutical products so prepared and to processes for the preparation thereof.

Below, the term "NASP" will be used for "natural antisecretory protein", whereas the term "ASP" will be used for "antisecretory protein" comprised by natural antisecretory protein.

PRIOR ART

From the Swedish Patent SE 9000028-2 (publication No. 466,331) it is known that the formation of an antisecretory factor or an antisecretory protein (ASP: also named FIL) can be stimulated by adding, to the animals' feed, certain sugars, amino acids and amides. The kinds and amounts of these substances to be used for the formation of an interesting amount of ASP is determined by a method disclosed in the patent. Briefly, this method involves measurement of a standardized secretion response in the small intestine of rat. From the patent is evident that the induced ASPs formed direct the secretion of body fluid into the intestine. Due to this, diarrhoea conditions may be prevented or cured which means a safer production of animal products. In said patent, the content or amount of natural antisecretory proteins is defined by its effect on the fluid secretion into the small intestine of laboratory rats having been challenged with cholera toxin. One ASP unit (FIL unit) corresponds to a 50% reduction of the fluid flow in the intestine compared to a control without ASP. The antisecretory proteins are active in extremely small amounts and, therefore, it is easier to determine them by their effect than by their mass.

From the PCT application PCT/SE96/01049 there are known the structures of certain antisecretory proteins, and their active parts are characterised. A synthetic ASP prepared by recombinant genetic engineering or by solid phase technology and having definite structures has been shown to have a general controlling influence on the body fluid flow over living cell membranes.

From the PCT application PCT/SE97/01918 (WO 98/21978) it is known that the formation of ASP can be induced in the body by consumption of a certain kind of food having enzymatic activity. The effect of the induction and, owing to that, the formation of ASP varies according to the individual and its symptoms and takes place with a strength and induction period unpredictable so far. However, they can be measured afterwards, and necessary corrections can be made with the guidance of said measurements.

BRIEF DESCRIPTION OF THE INVENTION

During the inventors' continued work in formulating feed to stimulate the formation of antisecretory proteins in accordance with Swedish Patent SE 9000028-2, it has surprisingly been found that the synthesis ability and concentrating of the natural antisecretory proteins formed are distributed most unevenly in the body. Very high levels of NASP are found in certain organs, body parts or body fluids and, in particular, in the yolk of birds' eggs. The present invention is based on this surprising fact and, consequently, relates to the use of egg yolk having been enriched with regard to NASP, for the preparation of NASP-enriched food products and pharmaceutical products for the treatment and prophylaxis of abnormal physiological conditions caused by extreme body fluid discharge. Thus, the invention opens possibilities, unknown so far, to administer NASP directly in the food or feed by consumption of the egg yolk as such or in the form of food products.

DETAILED DESCRIPTION OF THE INVENTION

The present invention generally relates to use of natural antisecretory proteins for the preparation of NASP-enriched functional food products and pharmaceutical products for the treatment and prophylaxis of abnormal physiological conditions caused by extreme body fluid discharge and, according to one aspect, relates to the use of egg yolk having been enriched with regard to NASP, for the preparation of food products having a high level of NASP. According to another aspect the invention relates to such use for the preparation of provisions for particular nutrient purposes and pharmaceutical products containing NASP.

By "functional food product" is meant, in the present context, a food product having a salubrious function, i.e. having a beneficial effect on the health of man or an animal.

The expression "food product" is intended, in the present context, to comprise food for human use as well as feed for animal use. The food can be an article in the form of products, the preparation of which includes egg yolk, such as pancake, omelet, ice-cream and various kinds of bread. The egg yolk may also be consumed in the form of egg-nog or hard-boiled or soft-boiled eggs. The food can also be in the form of bread, biscuits, pasta, grains and flakes, porridge or gruel, or mixed into various beverage compositions with or without electrolytes, or a food preparation containing meat and meat products, fat and fat products or milk and milk products having been enriched with NASP according to an embodiment of the invention described below, according to which NASP has been mixed into the food product in a more or less purified form. The food preparation can be made up with great liberty using knowledge known to the skilled man, in order to comply with requirements as regards palatability and meal variation.

The egg yolk originates from birds' eggs that can be used for human and animal consumption and having been enriched with regard to NASP. The eggs are preferably produced by laying hens but can also be obtained from e.g. quail and ostrich.

By "NASP-enriched food product" or "food product having a high level of NASP" are meant food products containing NASP in a concentration such that, when consuming the food product, provides the desired valuable effect on health. Particularly high levels of NASP can be measured in eggs, as is evident from Example 1. When consuming the NASP-enriched product it is seen to it that the ASP level in blood exceeds 0.5 FIL units/ ml of blood. Healthy people seem to have ASP levels in blood between 0 and 0.5 FIL units/ ml of blood.

When stimulating the NASP production according to SE 9000028-2, it has been shown, surprisingly and unexpectedly, that extremely high levels of NASP can be induced in birds' eggs. In blood, the NASP level, upon such an induction, normally is 0.5–2 FIL units/ml of blood (1 FIL unit=the amount of NASP providing a 50% inhibition of the fluid discharge in a so-called intestine loop test on rat; cf. SE 9000028-2 and references 3 and 4 cited therein). By providing the bird, via the feed, with distinct combinations of amino acids, sugars and amides, in accordance with SE 9000028-2, high levels of NASP can be built-up, preferably in the egg yolk. Levels as high as from about 1,000 to about 10,000 FIL units per ml are therewith provided. In this context, it should be mentioned that the NASP level in egg yolk normally, without a preceding induction, is about 1 FIL unit/ml; cf. S.Lange et al, *British Poultry Science* (1994) 35:615–620.

According to one embodiment of the use in accordance with the invention, NASP-enriched food products can be prepared by mixing NASP as such into the food, the NASP having been obtained in a more or less purified form from NASP-enriched egg yolk.

Thus, it is possible to stimulate the formation of NASP in a bird, as disclosed in SE 9000028-2, and then recover or concentrate NASP, also as disclosed in said Swedish Patent, from digests of egg yolk on an agarose column and thereupon eluate this with a solution of alpha-methylglycoside in physiological saline preferably phosphate-buffered. Thereupon, the eluate can be subjected to further purification and formulation before administration, e.g. in the form of a solution (sol).

In this case, the recovered or concentrated NASP can then be administered to animal or humans, mixed with a feed or food, respectively, or as more or less isolated products, prepared and formulated as pharmaceuticals or other health-providing products. Such pharmaceutical products are prepared in a manner known to the skilled man, using accepted excipients including carriers and diluents and are formulated as solid or liquid forms dependent on the intended administration route.

According to another embodiment of the use in accordance with the invention for the preparation of NASP-enriched food products, use is made of the egg yolk as such or of the complete egg, possibly in processed form, for mixing with the food or feed. Any processing can include grinding, leaching, extraction, evaporation, ultra-filtration, drying and other standard operations in order to obtain an NASP-enriched egg yolk product, suitable for practical purposes, for mixing with the food or feed.

According to the invention, novel routes are opened to achieve the favourable effects associated with NASP intake. The effect of NASP can be used due to the high concentration of NASP in egg yolk that can be induced, without awaiting the time delay caused by the previously known induction of NASP.

Thus, according to a further aspect the present invention relates to a process for providing egg yolk from birds' eggs being enriched with regard to NASP, the process being characterised by stimulating the formation of NASP by feeding the bird from which the eggs are to be taken with a NASP-inducing feed according to SE 9000028-2. In particular, the process of the invention is applicable when feeding gallinaceous birds because, as stated above, it has been shown, surprisingly and unexpectedly, that extremely high levels of NASP can be induced in eggs from said birds. By providing, via the feed, the hens with distinct combinations of amino acids, sugars and amides very high levels (about 100–1,000 FIL units) of NASP can be built-up, as also stated above, preferably in the egg yolk. Owing to this, there is opened the particular possibility of preparing egg yolk according to the invention disclosed in said patent, with extremely high levels of NASP. By mixing such egg yolk or products thereof into a food or feed, NASP can be added to humans or animals in a convenient, safe and cost-efficient way. It is thus very surprising and not previously known that such high levels of NASP can be achieved in provisions. Owing to this, the effect of NASP thus can be used, as mentioned above, without awaiting the time delay caused by the previously known induction of NASP. It is also surprising that NASP maintains its effect even when administered orally.

For certain conditions high doses of NASP may be required. In such cases, NASP recovered from egg can be added to the food product or NASP can be prepared for intake in the form of tablets or suspensions.

A particularly preferred embodiment comprises the preparation of egg yolk powder by spray-drying. Such a product is particularly well suitable in industrial processing of various food products where it is desired to achieve the beneficial effect of NASP upon intake of the food product in question. The egg yolk powder lets itself be well mixed into such greatly differing products as sausage and ice cream, owing to which a far-reaching variation as regards meal character will be possible to achieve.

The egg yolk powder is also most suitable as intermediate in case it is desired to prepare an enriched or concentrated NASP product through leaching or extraction for later preparation of e.g. pharmaceuticals.

Owing to its relatively low molecular weight, NASP is comparatively heat-stable and can therefore be contained in the food already before preparing the same for consumption.

NASP has been shown to have a generally controlling effect on the body fluid flow over living cell membranes, owing to which not only diarrhoea conditions can be alleviated, cured or prevented but also discomfort due to physiological unbalance or disease-like conditions caused by extreme body fluid discharge such as inflammations, oedema, arthritis, glaucoma and other changes in the body, such as migraine, burns and traumatic injuries in and on the body. The food products and the pharmaceutical products according to the invention can thus be used for such a purpose.

The invention is illustrated below by means of the following non-limiting examples.

EXAMPLE 1

Laying hens (white leghorn of about 32 weeks age) were fed with a laying hen feed composed according to SE 9000028-2 and with control feed of traditional type, 11.4 MJ/kg of feed, 170 g of raw protein per kg of feed. After an induction period of 2 weeks, eggs were collected.

From each line 10 eggs were collected, and the yolk and the white from these eggs were separated manually. Upon dilution with an equally large volume of PBS (phosphate-buffered saline) the yolk was subjected to affinity chromatography in accordance with a method described earlier (I. Lönnroth and S. Lange, *Biochimica Biophysica Acta* (1986) 883:138:144). Briefly, PBS-diluted egg yolk was applied on a small column containing "Sepharose 6B" (Pharmacia LKB Biotechnology AB, Sollentuna, Sweden) having been pre-equilibrated with PBS. Upon washing with PBS, NASP was eluated with methyl-alpha-D-glucoside, 1.0 M in PBS. After dialysis against PBS the sample was stored at $-20°$ C. until it was tested with regard to NASP according to the intestine loop model on rat described by Lange (S. Lange, *FEMS Microbiology Letters* (1982) 15:239,242.

| NASP level in egg yolk (FIL units /g) | |
| --- | --- |
| Control group | Test group |
| 1.20 | 2.0 (upon dilution 1:100) |
| | 1.0 (upon dilution 1:1,000) |

EXAMPLE 2

An ostomy-operated woman, 42 years of age, having a remain of about 0.5 m suffered badly from heavy diarrhoeas. In average, about 1.5 litres of visceral contents were secreted 4 times a day. After 1 week's daily intake of ice-cream, prepared from sugar, cream and egg yolks from Example 1, corresponding to a daily intake of 4 g of dry egg yolk substance, the defecation frequency decreased to once a day and the amount decreased to about 350 mls. During three-weeks' treatment the woman's weight increased by 3.5 kgs. After one further week, she ate the same amount of ice cream prepared from ordinary eggs according to the same recipe. Within three days, the defecation frequency and amount amounted to the same values as before the test. After one further week, the test was resumed, and within two days the defecation decreased to the same values as during the previous test.

EXAMPLE 3

Four calves having a living weight of 50 kgs were divided into two groups, each group containing two calves. The calves of the control group were supplied with calfs nutrient in the form of commercial milk substitute. In the test line, there was mixed-in egg yolk from the experiment of Example 1, corresponding to a daily dose of two egg-yolks. The feeding continued for seven days. The ASP level in blood was measured before and after the experiment.

| ASP level (FIL units/ml of plasma) | | |
| --- | --- | --- |
| | Control group | Test group |
| Before experiment | 0.3 | 0.1 |
| After experiment | 0.1 | 0.9 |

EXAMPLE 4

Diarrhoea is not an unusual complaint in dogs, particularly in such dogs having the possibility of choosing themselves, during airing in the country, their intake of food. Such a male German shepherd dog of 1.5 years of age and having a weight of about 40 kgs suffered, for some time, from heavy diarrhoea and watery and periodically bloody defecation. The dog also vomited intermittently. The veterinary was sent for and prescribed antibiotics to be taken orally in the form of tablets for one week. During this period the dog ate less amounts of commercial dry fodder for dogs. No decrease of the diarrhoeas was observed. After this antibiotic treatment the dog was provided with soaked dry fodder in which egg yolk powder from Example 6 in an amount corresponding to one egg yolk a day, for four days. After one day and night the dog had solid defecation and, after three days, he was considered perfectly healthy. At no time earlier, the dog's owner had observed such a fast recovery.

EXAMPLE 5

Eggs from the test line in Example 1 were cracked and separated in an egg separation apparatus. Egg yolk and egg white were collected each separately. The egg yolk was spray-dried in an "Anhydro" spray-dryer with an inlet temperature of 150° C. and an outlet temperature of about 75° C.

The egg powder was collected and, upon completed drying, the powder adhering to the walls of the spray-drier was collected. These wall depositions had an average residence time in the drying chamber of 4 hours. The egg powder was dissolved in water and ASP was collected, in a known way, on an agarose column. The eluate was diluted and its ASP contents were measured.

| FIL units upon dilution 1:100 | |
| --- | --- |
| Egg powder, average sample | X |
| Egg powder from drying chamber wall | Y |

Thus, from a food technology point of view, NASP is sufficiently heat-stable.

TECHNICAL EFFECT

By the present invention, entirely novel and previously unknown possibilities are provided to administer NASP with entirely novel, previously unknown degrees of independence. The induction of NASP disclosed in the PCT application PCT/SE97/01918 (WO 98/21978) may be difficult to maintain for a long time owing to the fact that the diet is easier perceived as monotonous. By the present discovery, food products of high palatability and good acceptance can be prepared with moderate process costs. In case of long courses of disease or weak response to NASP-inducing food, NASP can be administered in the form of provisions having a predetermined higher or lower dose adapted to the desired effect on quality of life or physical performance efficiency. In case of long-lasting administration, loathing for (disgust with) the food can be avoided because a great number of products can be prepared having varied taste and meal character. The food products can be prepared industrially as semi-manufactured foods or finished meals or as articles suitable as raw product in the preparation of pharmaceuticals or in the manufacturing of NASP concentrates. The concentrate can be recovered from egg yolk or preferably from egg yolk powder by extraction or leaching.

What is claimed is:

1. An egg yolk having a food induced high level of natural anti-secretory protein (NASP), wherein said egg yolk has a NASP content corresponding to at least 1,000 FIL units/ml.

2. The egg yolk of claim 1 having a NASP content corresponding to 1,000–10,000 FIL units/ml.

3. The egg yolk of claim 1 originating from eggs of gallinaceous birds.

4. A process for obtaining egg yolk having a food-induced high level of natural anti-secretory protein (NASP) from an egg-producing bird, wherein the egg yolk is enriched with NASP, comprising feeding the bird with an effective amount of a NASP-inducing feed such that said egg yolk obtained from the egg-producing bird has a NASP content corresponding to at least 1,000 FIL units/ml.

5. The process according to claim 4, wherein the NASP induction has been effected by mixing, into the feed of the bird, amino acids, sugars and amides in amounts and proportions such that the formation of NASP has been stimulated.

6. The process according to claim 4, wherein the NASP induction has been effected by mixing, into the feed of the bird, products having enzymatic activity stimulating the formation of NASP.

7. The process according to claim 6, wherein the products having enzymatic activity are malted cereals.

8. The process of claim 4, wherein the bird is a gallinaceous bird.

9. The process of claim 4, wherein the NASP-inducing feed contains amino acids, sugars and amides in an amount such that the formation of NASP is stimulated.

10. The process of claim 4, wherein the feed contains products having enzymatic activity stimulating the formation of NASP.

11. The process of claim 10, wherein the products having enzymatic activity are malted cereals.

* * * * *